United States Patent
Kim et al.

(10) Patent No.: US 9,808,195 B2
(45) Date of Patent: Nov. 7, 2017

(54) 2D SCANNING VIDEOKYMOGRAPHY SYSTEM FOR ANALYZING VIBRATION OF VOCAL-FOLD MUCOSA, AND METHOD OF ANALYZING VIBRATION OF VOCAL-FOLD MUCOSA USING THE SAME

(71) Applicants: Tae Woo Kim, Gangwon-Do (KR); Yong Jin Wang, Busan (KR)

(72) Inventors: Tae Woo Kim, Gangwon-Do (KR); Yong Jin Wang, Busan (KR)

( * ) Notice: Subject to any disclaimer, the term of this patent is extended or adjusted under 35 U.S.C. 154(b) by 66 days.

(21) Appl. No.: 14/775,734

(22) PCT Filed: Oct. 10, 2013

(86) PCT No.: PCT/KR2013/009052
§ 371 (c)(1),
(2) Date: Sep. 14, 2015

(87) PCT Pub. No.: WO2014/148712
PCT Pub. Date: Sep. 25, 2014

(65) Prior Publication Data
US 2016/0000370 A1 Jan. 7, 2016

(30) Foreign Application Priority Data
Mar. 21, 2013 (KR) .................. 10-2013-0030086

(51) Int. Cl.
*A61B 6/00* (2006.01)
*A61B 5/00* (2006.01)
(Continued)

(52) U.S. Cl.
CPC ........ *A61B 5/4803* (2013.01); *A61B 1/00006* (2013.01); *A61B 1/00009* (2013.01);
(Continued)

(58) Field of Classification Search
CPC ... A61B 5/4803; A61B 5/0084; A61B 1/2673; A61B 1/0661; A61B 1/00009; A61B 1/00
See application file for complete search history.

(56) References Cited

U.S. PATENT DOCUMENTS

2005/0219376 A1  10/2005  Wittenberg et al.
2006/0235693 A1  10/2006  Ruderman et al.
(Continued)

FOREIGN PATENT DOCUMENTS

KR  10-1999-0079315 A  11/1999
KR  10-2005-0018884 A  2/2005

OTHER PUBLICATIONS

International Search Report issued in corresponding application No. PCT/KR2013/009052 dated Feb. 26, 2014 (2 pages).

*Primary Examiner* — Robert N Wieland
(74) *Attorney, Agent, or Firm* — Osha Liang LLP

(57) ABSTRACT

Disclosed is a 2D scanning videokymography system for analyzing a vibration of vocal-fold mucosa, including: a laryngoscope for observing vocal folds; a light source for illuminating the vocal folds; a video camera for recording and storing images observed through the laryngoscope; a computer incorporating an image capture unit for converting a video signal transmitted from the video camera into a digital image signal, a storage unit for storing the digital image signal, a control unit for analyzing the image signal of the storage unit and displaying the analysis results on a monitor, and analysis software for analyzing the image signal of the storage unit; and a monitor for displaying a captured image and analysis results.

6 Claims, 14 Drawing Sheets

(51) Int. Cl.
*A61B 1/04* (2006.01)
*A61B 1/267* (2006.01)
*A61B 1/00* (2006.01)
*A61B 5/11* (2006.01)
*A61B 1/06* (2006.01)

(52) U.S. Cl.
CPC .............. *A61B 1/04* (2013.01); *A61B 1/2673* (2013.01); *A61B 5/0062* (2013.01); *A61B 5/0084* (2013.01); *A61B 5/1128* (2013.01); *A61B 1/00045* (2013.01); *A61B 1/0661* (2013.01)

(56) References Cited

U.S. PATENT DOCUMENTS

| | | | | |
|---|---|---|---|---|
| 2009/0281390 | A1* | 11/2009 | Qiu | A61B 1/2673 600/199 |
| 2012/0150293 | A1* | 6/2012 | Hoffman | A61F 2/20 623/9 |
| 2014/0316196 | A1* | 10/2014 | Wichern | A61B 1/05 600/109 |

* cited by examiner

[FIG. 1]
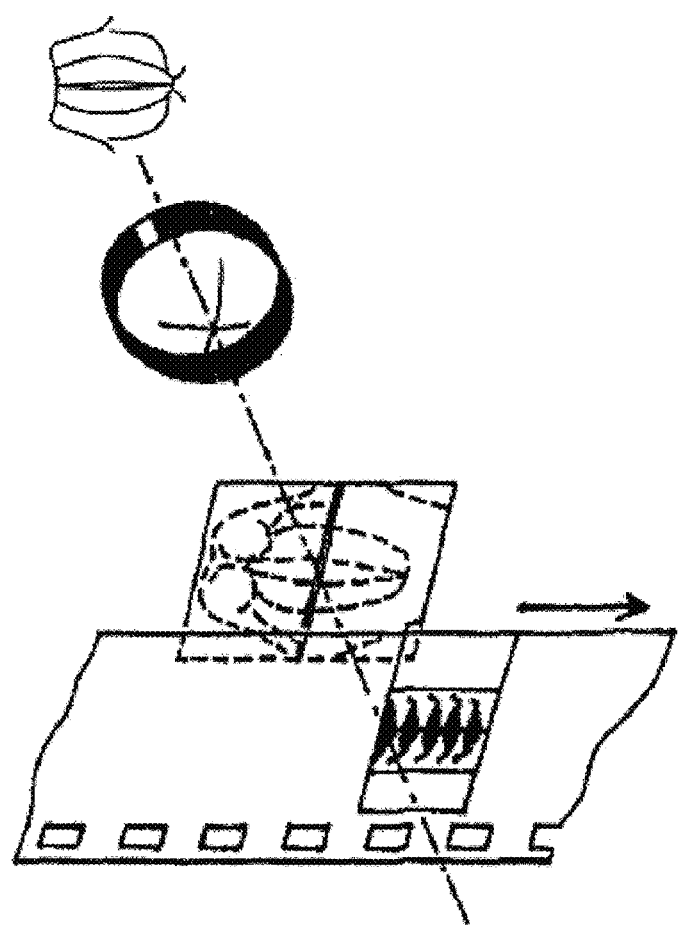

[FIG. 2]
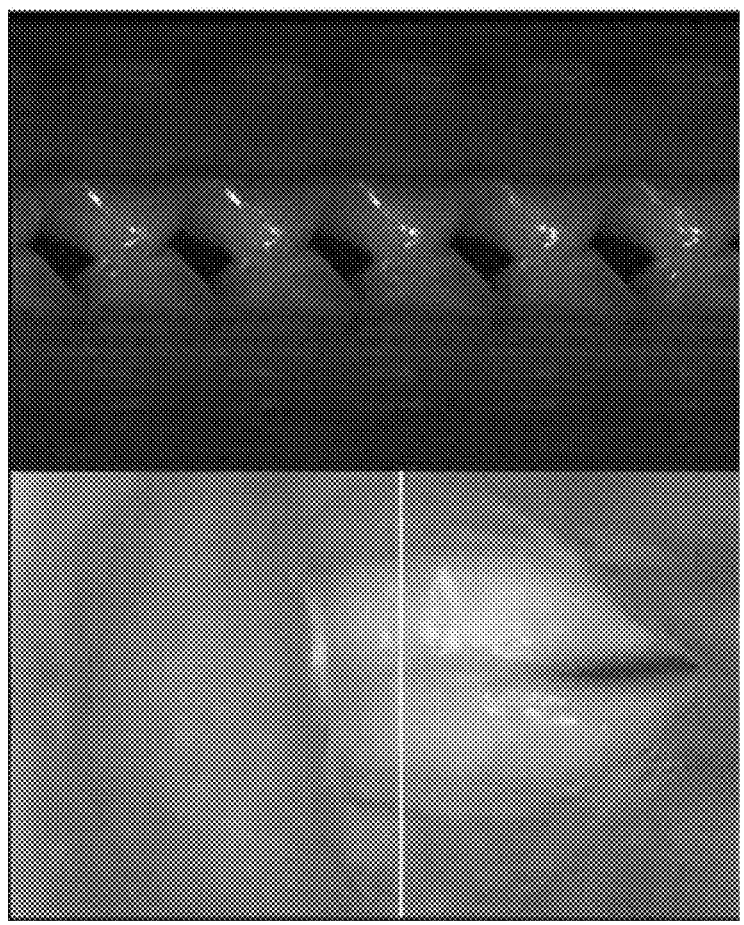

[FIG. 3]
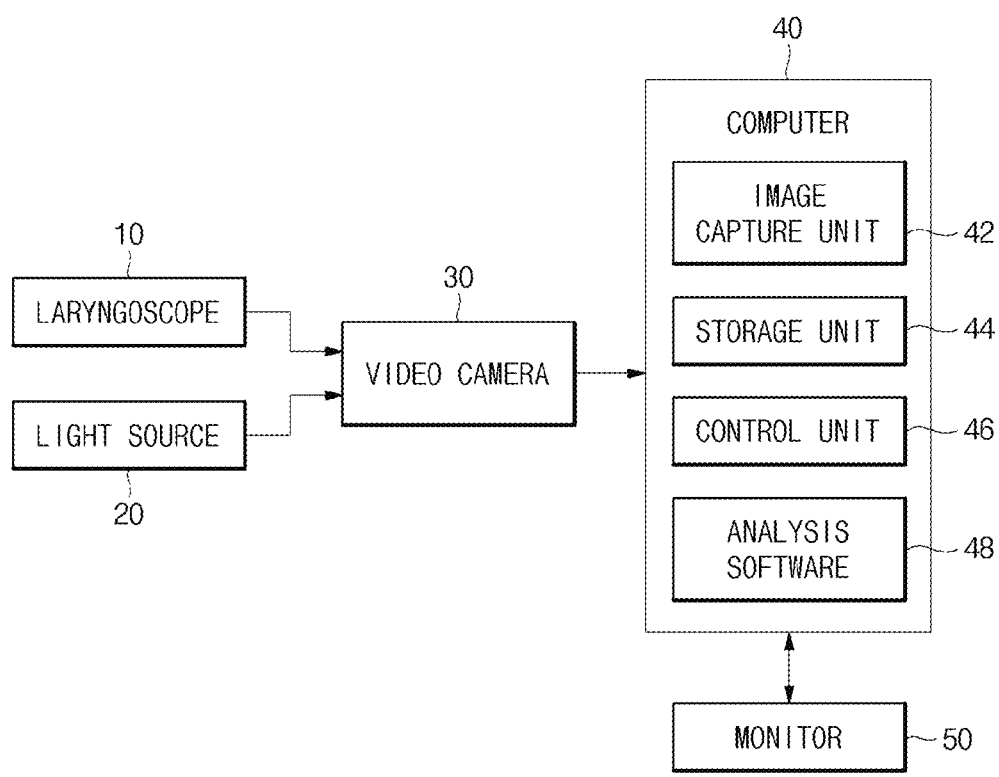

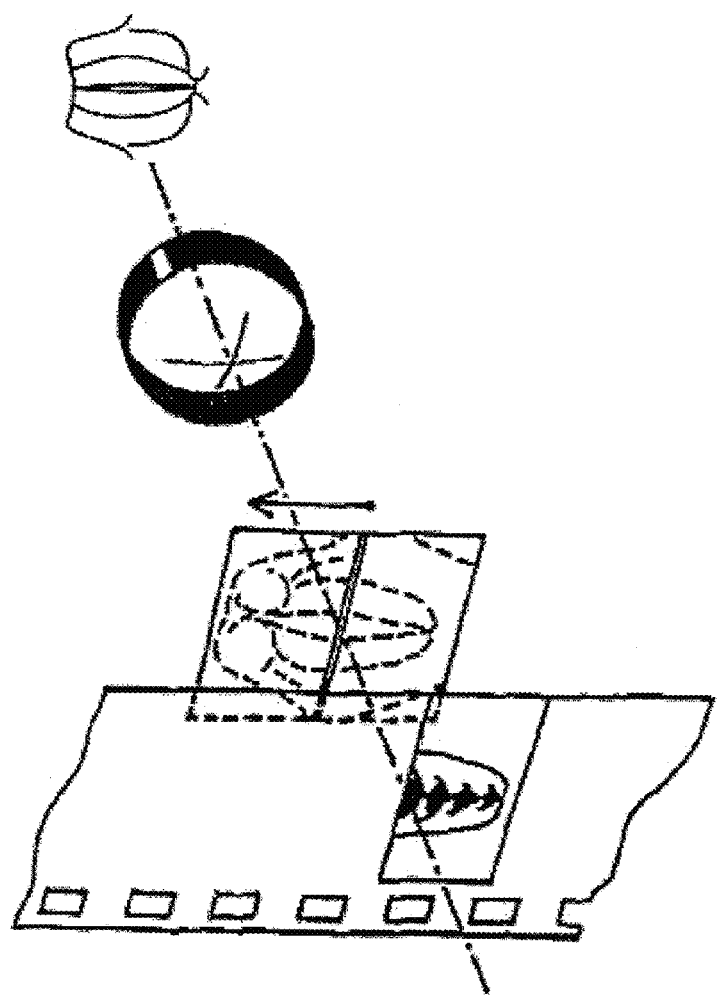
[FIG. 4]

[FIG. 5A]
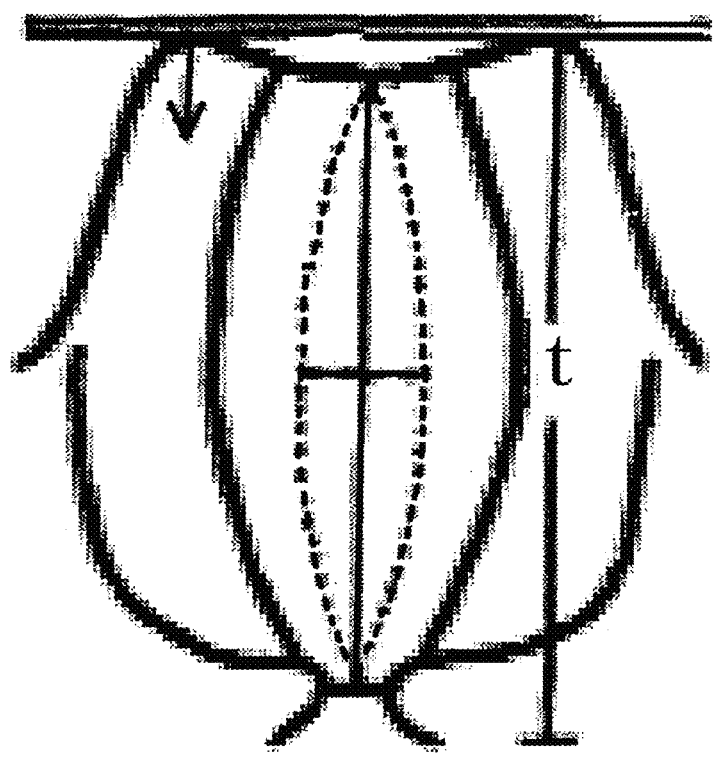

[FIG. 5B]
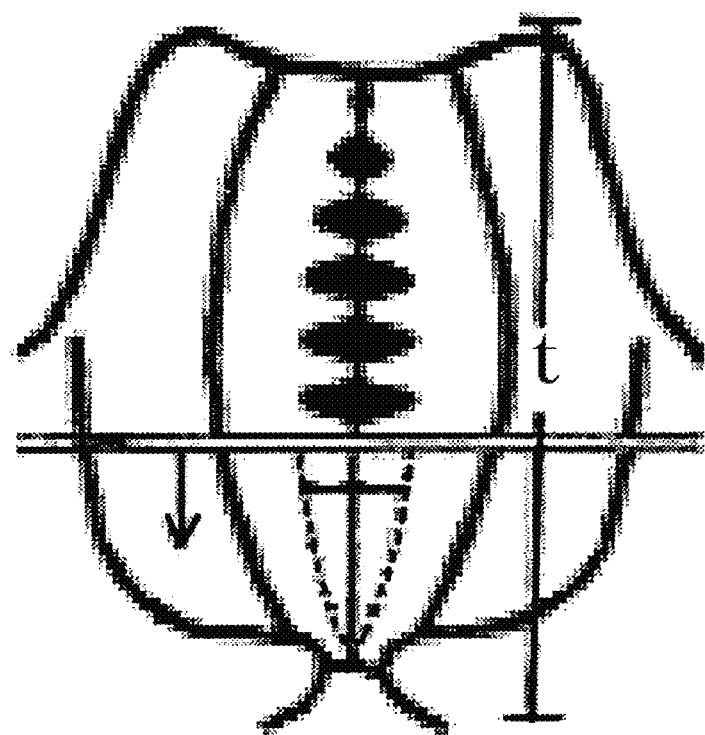

[FIG. 5C]
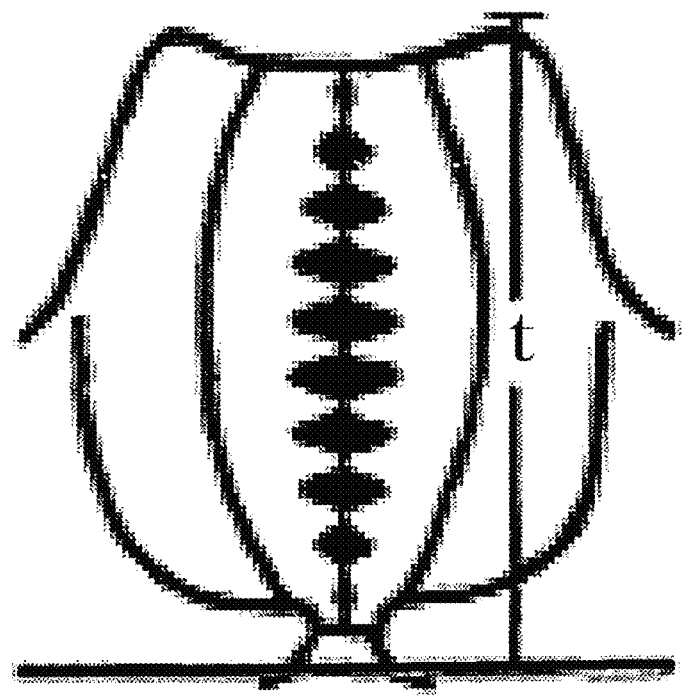

[FIG. 6]
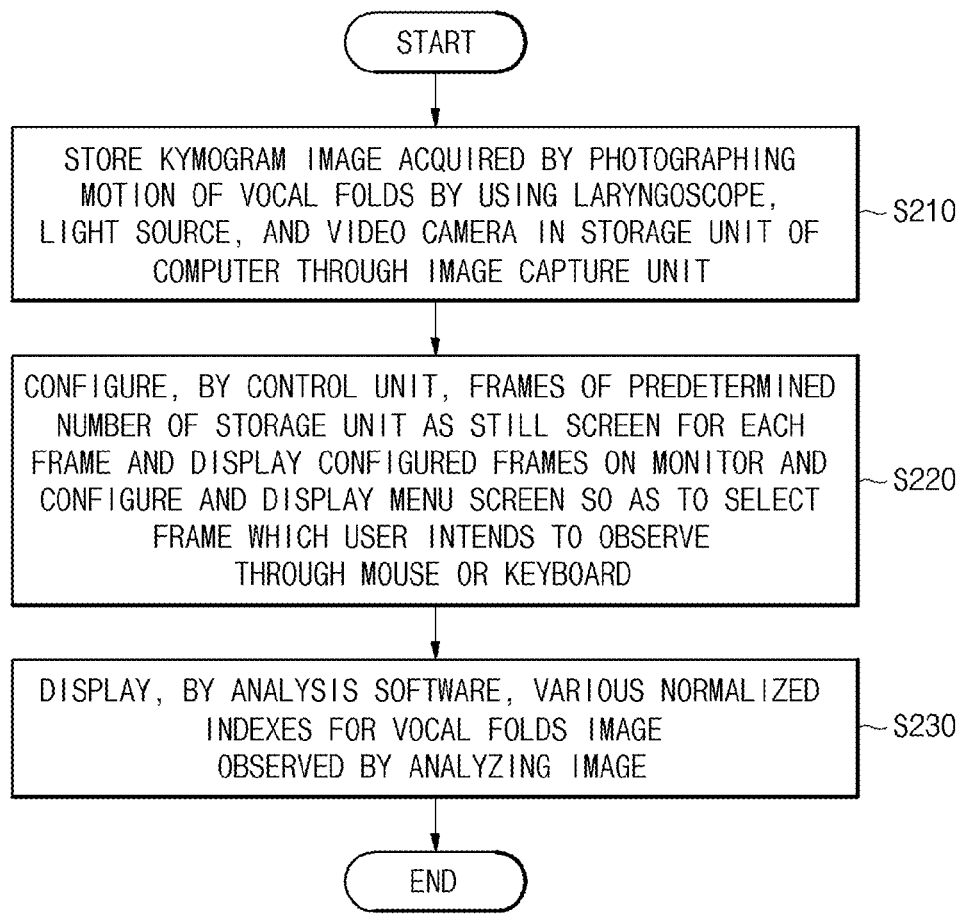

[FIG. 7]
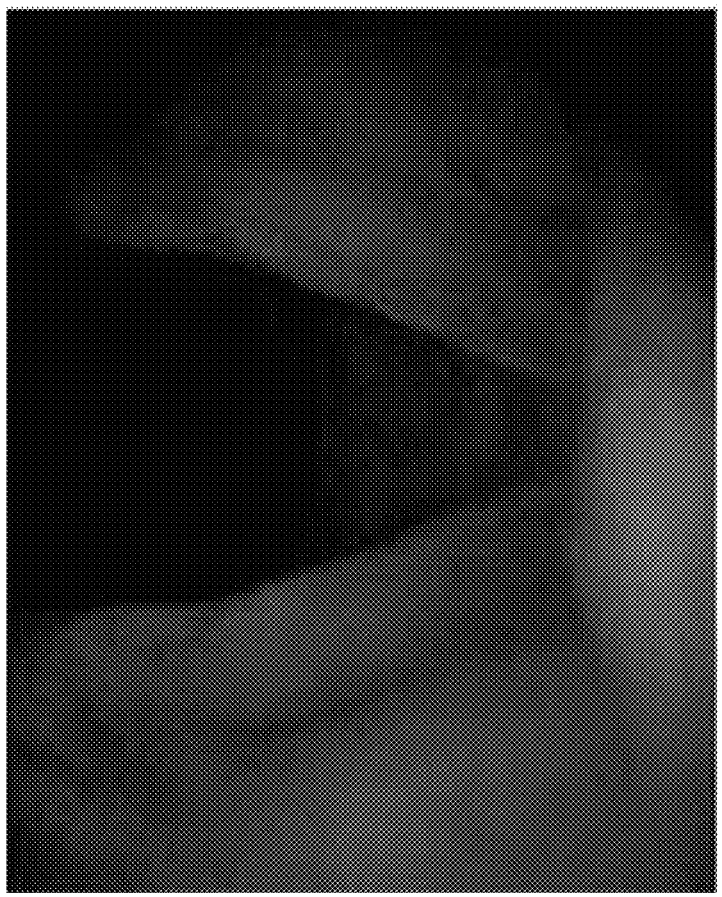

[FIG. 8]

[FIG. 9]

[FIG. 10]

[FIG. 11A]
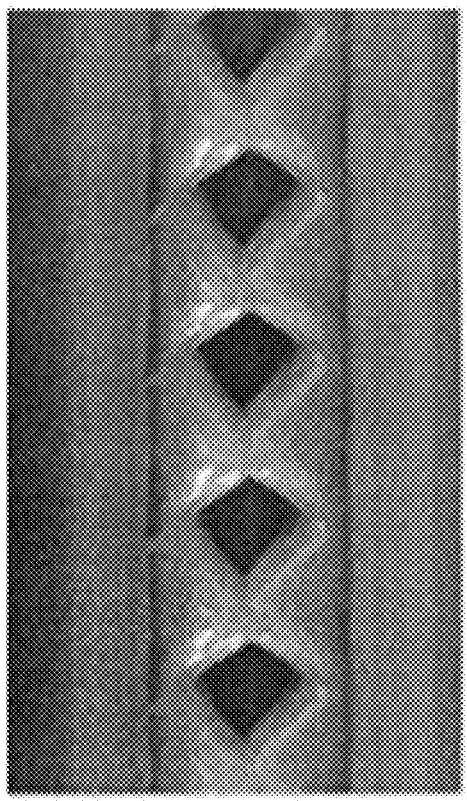

[FIG. 11B]
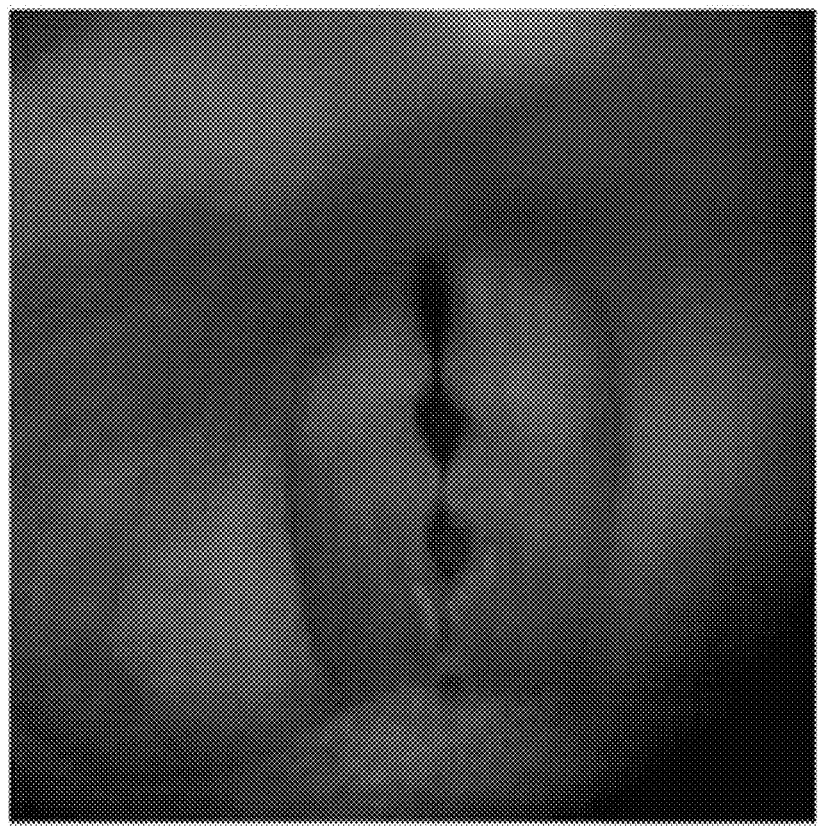

2D SCANNING VIDEOKYMOGRAPHY SYSTEM FOR ANALYZING VIBRATION OF VOCAL-FOLD MUCOSA, AND METHOD OF ANALYZING VIBRATION OF VOCAL-FOLD MUCOSA USING THE SAME

TECHNICAL FIELD

The present invention relates to a videokymography system for analyzing a state of a vocal-fold mucosa, and to a 2D scanning videokymography system and an analyzing method thereof which can extract a vibration state of not a part of a vocal fold but an entire area of the vocal fold in real time and analyze a vibration of a mucosa of the entire area of the vocal fold.

BACKGROUND ART

The larynx is a vocal organ for communication through a language and vocal folds in the larynx vibrate approximately 100 to 350 times per second with the flow of air of breathing exhaled during vocalization. However, in a disease state in which a voice is changed, a motion of a vocal-fold mucosa is irregular and asymmetric or the vibration decreases and in a severe disease state, the vibration may disappear.

The pressure of air inhaled into a lower airway during the vocalization increases by the vocal folds which are closed at a lower part of a glottis and when the pressure becomes larger than resistance of the vocal folds, the vocal folds are opened while the flow of air that goes from an inferior margin to a superior margin of the vocal folds is formed. A mucosa wave is generated in the vocal-fold mucosa by the flow of the air and a characteristic of a speed or the strength of the mucosa wave determines the quality of a voice. That is, the vocal folds serve to convert sub-glottal pressure generated at a lower portion of the glottis into sound energy while symmetrically vibrating at tens to hundreds of Hz. However, when vocal fold nodules or vocal fold paralysis is caused, symmetricity of the mucosa wave deteriorates and effective conversion of energy becomes impossible to cause trachyphonia (harsh sounds).

Therefore, when abnormality of the voice is examined, determining the vibration of the vocal-fold mucosa, that is, the vibration of the vocal folds is required. To this end, one of methods which are currently used is a laryngeal stroboscope. A method that uses laryngeal videostroboscopy to observe a rapid motion of 100 to 350 times per second of the vocal folds as a slow motion by using the laryngeal stroboscope is primarily used. However, there is a fundamental problem that an image which can be observed through the laryngeal videostroboscopy is an image that does not show vibration of the vocal folds having an actually accurate cycle (period) but is generated by combining some of various cycles. Moreover, meaningful analysis is impossible in a patient having aperiodic dysphonia in which variations among respective periods of the motion of the vocal folds are large or periodic repetitiveness is absent while a gap between the vocal folds is large during the vocalization, and as a result, an overall motion of the vocal-fold mucosa is only qualitatively described. Further, there is a problem to be solved, in that a detailed motion of a part or the entirety or a specific part of the vocal-fold mucosa cannot be individually identified, or the like. In addition, since the image of the laryngeal stroboscopy is only quietly subjectively observed, determination of a skilled experienced person is required for accurate analysis.

As another vocal fold vibration examining method for overcoming a disadvantage, a line scanning videokymography technique has been developed by Svec J G, Schutte H K in 1996. This method is a method that acquires an image for a motion on a consecutive line of approximately 8000 frames per second with respect to a part of the vocal fold arbitrarily selected by an examiner during the examination, that is, one line and displays the acquired image on a monitor. That is, as illustrated in FIG. 1, a part of the vocal folds having a slit is rapidly photographed to photograph a motion of only the part. However, the disadvantage thereof is not observation of the entire vocal folds but evaluation of a part of one line. That is, when an examinee makes vocalization once, only kymogram for one line can be acquired and since a motion of an entire area cannot be observed while acquiring Kymogram, there are problems in that there is no criterion to normally judge distortion by a motion of a patient, and like.

Besides, a method using multi-line videokymography by readjusting an image photographed by an ultra-high speed digital imaging method is also present, but is the same as line videokymography in that the entirety of the vocal folds is not observed and subsidiary equipment such as a high-priced CCD camera which is particularly devised is required, and as a result, there are a lot of limitations in use.

DISCLOSURE

Technical Problem

The present invention has been made in an effort to provide a 2D scanning videokymography system and an analyzing method thereof which can extract a vibration state of not a part of a vocal fold but an entire area of the vocal fold in real time and analyze a vibration of a mucosa of the entire area of the vocal fold.

Technical Solution

An exemplary embodiment of the present invention provides a 2D scanning videokymography system for analyzing a vibration of vocal-fold mucosa, including: a laryngoscope for observing vocal folds; a light source for illuminating the vocal folds; a video camera for recording and storing images observed through the laryngoscope; a computer incorporating an image capture unit for converting a video signal transmitted from the video camera into a digital image signal, a storage unit for storing the digital image signal, a control unit for analyzing the image signal of the storage unit and displaying the analysis results on a monitor, and analysis software for analyzing the image signal of the storage unit; and a monitor for displaying a captured image and analysis results.

The video camera may scan the vocal-fold mucosa with a rolling shutter to acquire 2D scanning videokymography and a shutter speed of the video camera may be set to $1/1000$ seconds or more.

The light source may be a Xenon continuous light source.

Another exemplary embodiment of the present invention provides an analysis method of a vibration of vocal-fold mucosa, which is performed in a 2D scanning videokymography system, the method including: (a) storing a kymogram image acquired by photographing the motion of the vocal folds by using a laryngoscope, a light source, and a video camera in a storage unit through an image capture unit; (b) configuring, by a control unit, image frames of a predetermined number of the storage unit as a still screen for each frame and displaying the configured frames on a monitor and configuring and displaying a menu screen so as to select a frame which a user intends to observe through a mouse or a keyboard; and (c) displaying, by analysis software, a normalized index for the vocal folds observed by analyzing an image.

In this case, in step (a), an entire part of the vocal folds may be photographed without vocalization and thereafter, "i" or "e" may be vocalized and the motion of the entire part of a vocal-fold vibration part may be photographed.

Preferably, in step (c), the normalized index may include an average vocal-fold width for a longitudinal-axis length of a glottis, a glottis opening ratio which is a ratio of a vocal-fold opening period and a total period, an asymmetric index which is a difference in opening degree of both vocal folds, a basic frequency, a vibration strength, regularity of vibration, a mucosa wave, symmetricity of the vibration, an outer boundary shape, an inner boundary shape, an abnormal cycle, or vibration absence of the vocal-fold mucosa.

Advantageous Effects

According to exemplary embodiments of the present invention, by departing from the existing method that analyzes a video image which is already stored and a real-time line scanning method that can observe only one line of vocal folds, kymogram in an entire area of the vocal folds can be compared in real time by using a 2D scanning videokymography system, and as a result, diagnosis of a motion of vocal-fold mucosa and subsequent prognosis tracking are easy. Further, a 2D kymography image is stored, and as a result, an examiner can carefully and repeatedly observe an image through a video to objectively analyze indexes including a basic frequency which is a more accurate and meaningful parameter, a mucosa wave, symmetricity of vibration, a vibration strength, regularity of the vibration, a phase difference, absence of vibration of the vocal fold, interference of surroundings with the vocal folds, duration of glottal closure, left-right asymmetry, presence of mucosal waves, type of cycle-to-cycle variability, left-right asymmetry, shapes of the lateral and medial peaks, cycle aberrations, and the like and preserve an examination result. Moreover, the normalized indexes according to the present invention are useful to visualize and quantify the vibration state of the vocal folds to objectively evaluate a laryngeal function.

DESCRIPTION OF DRAWINGS

FIG. 1 is a schematic view for describing a principle of line scanning videokymography in the related art.

FIG. 2 is an image screen photographed by a line scanning videokymography system in the related art.

FIG. 3 is a schematic block diagram of a 2D scanning videokymography system according to an exemplary embodiment of the present invention.

FIGS. 4 and 5 are schematic views for describing a principle of 2D scanning videokymography used in the present invention, and FIG. 4 illustrates a principle of entire vocal folds, that is, 2D scanning and FIG. 5 illustrates an image of the entire vocal folds which are 2D Scanned.

FIG. 6 is a flowchart for describing an analysis method of a vibration of vocal-fold mucosa by the 2D scanning videokymography system according to another exemplary embodiment of the present invention.

FIG. 7 illustrates an image screen of a laryngendoscope of a normal person.

FIGS. 8 to 10 illustrate an image screen of a normal adult man photographed by the 2D scanning videokymography system according to the present invention, and FIG. 8 illustrates an opinion in low pitch voice, FIG. 9 illustrates an opinion in normal voice, and FIG. 10 illustrates an opinion in falsetto voice.

FIG. 11 illustrates comparison images of (a) the line scanning videokymography in the related art and (b) the 2D scanning videokymography according to the present invention.

BEST MODE

Hereinafter, exemplary embodiments according to the present invention will be described in detail with reference to the accompanying drawings. However, the following exemplary embodiments are provided for those skilled in the art to sufficiently appreciate the present invention, and various modifications of the present invention can be made and the scope of the present invention is not limited to the exemplary embodiments described below.

FIG. 3 is a schematic block diagram of a 2D scanning videokymography system according to an exemplary embodiment of the present invention. The 2D scanning videokymography system for analyzing the vibration of vocal-fold mucosa according to the exemplary embodiment of the present invention includes a laryngoscope 10, a light source, a video camera 30, a computer 40, and a monitor 50.

In a configuration of FIG. 3, the laryngoscope 10 as a tool that may observe vocal folds allows an image of the vocal folds to be photographed in connection with the video camera 30. As the laryngoscope, both a rigid type and a curved type may be used.

The video camera 20 is a device for recording and storing the image observed from the laryngoscope 10. In the present invention, the video camera is not a line scanning kymography method in the related art and extracts 2D scanning kymography. FIGS. 4 and 5 are diagrams for describing a principle of 2D scanning videokymography used in the present invention. As illustrated in FIG. 4, for the 2D scanning videokymography, the vocal-fold mucosa is scanned through a gap of a movable slit while the video camera stops to scan the entire vocal folds, that is, 2D scanning the entire vocal folds. In detail, as illustrated in FIG. 5, a thin slit shutter moves on a plane of the image of the vocal folds and a film is exposed during the movement. Since the image acquired through such a procedure is shown as one entire image generated by sequentially making multiple image rows generated by capturing an entire image of the larynx in different temporal steps, a dynamic image of the entire larynx is shown.

To this end, the video camera as a high-resolution type includes a rolling shutter. Preferably, the video camera may adopt a rolling shutter type CMOS camera module and a shutter speed may be set to a high speed of $1/1000$ sec. or more in order to increase the resolution of the image. In this case, since a screen may be very dark, a high-sensitivity and high-luminance light source is used as the light source 20 in order to brighten the screen. Preferably, as the light source 20 that illuminates the vocal folds, a very bright Xenon light source is used. Further, in the present invention, as the light source 20, not an intermittent light source (strobo light source) used in the existing stroboscope method but a continuous light source is used.

Normal persons or patients having an abnormal vocal-fold function are allowed to vocalize a specific sound ("I" or "e") in a comfortable state to photograph the vocal folds by using the laryngoscope 10, the light source 20, and the rolling shutter camera 30. Therefore, moving pictures of the predetermined number, for example, 30 continuous frames per second are recorded as an image recorded in a predetermined format, for example, an AVI method and the recorded moving pictures are replayed and output.

The computer 40 as a general personal computer includes an image capture unit 42, a storage unit 44, a control unit 46, and analysis software 48. The image capture unit 42 as a form of an image capture board serves to convert a video signal transmitted from the video camera 30 into a digital image signal which may be processed by the computer 40 and may adopt a general image signal processing board in which various images may be easily edited. In general, an auxiliary substrate type which may be inserted into a body substrate extension bus of the computer 40 in a slot form may be used.

The control unit 46 of the computer 40 stores the digital image signal of 30 continuous frames per second, which is transmitted from the image capture unit 42 in the storage unit 44 and thereafter, controls the analysis software 48 for analyzing the vibration of the vocal-fold mucosa. That is, the control unit 46 analyzes the image signal transported to the storage unit 44 to visualize an analysis result, that is, a vibration state of the vocal folds on the monitor 50 and display a quantified clinical index.

Next, an analysis method of the vibration of the vocal-fold mucosa according to another exemplary embodiment of the present invention in the 2D scanning videokymography system having the aforementioned configuration will be described in detail with reference to the accompanying drawings.

FIG. 6 is a flowchart for describing an analysis method of a vibration of vocal-fold mucosa by the 2D scanning videokymography system according to another exemplary embodiment of the present invention. Referring to FIG. 6, first, a kymogram image acquired by photographing the motion of the vocal folds by using the laryngoscope 10, the light source 20, and the rolling shutter type video camera 30 is stored in the storage unit 44 of the computer 40 through the image capture unit 30 (step 210).

In order to analyze the vibration of the vocal-fold mucosa, for example, an entire part of the vocal folds is photographed without vocalization and thereafter, "i" or "e" is vocalized and the motion of the entire part of a vocal-fold vibration part is photographed to be converted into the 2D scanning kymogram.

Next, the control unit 46 of the computer 40 configures frames of a predetermined number of the storage unit 44 as a still screen for each frame and displays the configured frames on the monitor and configures and displays a menu screen so as to select a frame which a user intends to observe through a mouse or a keyboard (step 220).

Next, the analysis software 48 of the computer 40 analyzes the image to normalize and display various indexes normalized with respect to the observed vocal folds, for example, an average vocal-fold width for a longitudinal-axis length of a glottis, a glottis opening ratio which is a ratio of a vocal-fold opening period and a total period, an asymmetric index which is a difference in opening degree of both vocal folds, a basic frequency, a vibration strength, regularity of vibration, symmetricity of the vibration, a mucosa wave, an outer boundary shape, an inner boundary shape, an abnormal cycle, vibration absence of the vocal-fold mucosa, and the like (step 230). Objective state evaluation may be achieved by using the various indexes.

Hereinafter, referring to FIGS. 7 to 11, the image acquired by the 2D scanning videokymography system according to the present invention will be described through comparison with the related art.

FIG. 7 illustrates an image screen of a laryngeal stroboscope of a normal person and FIGS. 8 to 10 illustrate an image screen photographed by the 2D scanning videokymography system according to the present invention. In FIGS. 8 to 10 which illustrate a 2D scanning kymogram image screen during vocalization of the normal adult man, 30 continuous frames of a vide image stored in a digital format (constituted by 30 frames per second as an NTSC image signal, that is, 60 fields) are transported to the computer storage unit by using the image capture unit and thereafter, displayed on the monitor.

In detail, FIG. 8 is a 2D scanning kymogram image screen during low-voice vocalization of a normal man, FIG. 9 is a 2D scanning kymogram image screen during normal vocalization of the normal man, and FIG. 10 is a 2D scanning kymogram image screen during falsetto voice vocalization of the normal man.

FIG. 11 illustrates comparison images of (a) the line scanning videokymography in the related art and (b) the 2D scanning videokymography according to the present invention.

FIG. 11A illustrates line scan kymography that photographs a motion of one part of the vocal folds. A disadvantage of (a) which is the image in the related art is not observation of the entire vocal folds but evaluation of a part on one line. That is, when an examinee makes vocalization once, only kymogram for one line can be acquired and since a motion of an entire area cannot be observed while acquiring kymogram, there are problems that there is no a criterion to normally judge distortion by a motion of a patient, and like. FIG. 11B illustrates a 2D scanning kymography image according to the present invention, which photographs the motion of the entire part of the vocal folds. According to the image of FIG. 11B, since the motion of the entire vocal folds may be observed in real time by remedying the disadvantage of the image of FIG. 11A, distortion by the motion of the patient, and the like may be minimized.

The invention claimed is:

1. A 2D scanning videokymography system for analyzing a vibration of vocal-fold mucosa, comprising:
    a laryngoscope for observing vocal folds;
    a light source for illuminating the vocal folds;
    a video camera for recording and storing images observed through the laryngoscope;
    a computer comprising an image capture unit for converting a video signal transmitted from the video camera into a digital image signal, a storage unit for storing the digital image signal, a control unit for analyzing the image signal of the storage unit and displaying the analysis results on a monitor, and analysis software for analyzing the image signal of the storage unit; and
    a monitor for displaying a captured image and analysis results,
    wherein the computer displays a normalized index including an average vocal-fold width for a longitudinal-axis length of a glottis, a glottis opening ratio which is a ratio of a vocal-fold opening period and a total period, an asymmetric index which is a difference in opening degree of both vocal folds, a basic frequency, a vibration strength, regularity of vibration, a mucosa wave, symmetricity of the vibration, an outer boundary shape, an inner boundary shape, an abnormal cycle, and vibration absence of the vocal-fold mucosa.

2. The system of claim 1, wherein the video camera scans the vocal-fold mucosa with a rolling shutter to acquire 2D scanning videokymography.

3. The system of claim 1, wherein a shutter speed of the video camera is set to $\frac{1}{1000}$ seconds or more.

4. The system of claim 1, wherein the light source is a Xenon continuous light source.

5. An analysis method of a vibration of vocal-fold mucosa, which is performed in a 2D scanning videokymography system according to claim 1, the method comprising:
   (a) storing a 2D scanning kymogram image acquired by photographing the motion of the vocal folds by using a laryngoscope, a light source, and a video camera in a storage unit through an image capture unit;
   (b) configuring, by a control unit, a predetermined number of image frames stored in the storage unit as a still screen for each frame and displaying the configured frames on a monitor and configuring and displaying a menu screen so as to select a frame which a user intends to observe through a mouse or a keyboard; and
   (c) displaying, by analysis software, a normalized index for the vocal folds observed by analyzing an image.

6. The method of claim 5, wherein in step (a), an entire part of the vocal folds is photographed without vocalization and thereafter, "i" or "e" is vocalized and the motion of the entire part of a vocal-fold vibration part is photographed.

* * * * *